US009388307B2

(12) United States Patent
Li et al.

(10) Patent No.: US 9,388,307 B2
(45) Date of Patent: Jul. 12, 2016

(54) MICROCUP COMPOSITIONS

(71) Applicant: SiPix Imaging, Inc., Fremont, CA (US)

(72) Inventors: Yu Li, Fremont, CA (US); HongMei Zang, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 467 days.

(21) Appl. No.: 13/686,778

(22) Filed: Nov. 27, 2012

(65) Prior Publication Data
US 2014/0147478 A1    May 29, 2014

(51) Int. Cl.
| C09K 19/00 | (2006.01) |
| C08L 33/06 | (2006.01) |
| C08L 33/14 | (2006.01) |
| G02F 1/167 | (2006.01) |
| C09J 133/14 | (2006.01) |
| B32B 7/06 | (2006.01) |
| B32B 7/12 | (2006.01) |
| B32B 27/06 | (2006.01) |
| B32B 27/16 | (2006.01) |
| B29C 39/02 | (2006.01) |
| B29C 59/02 | (2006.01) |

(52) U.S. Cl.
CPC . C08L 33/06 (2013.01); B32B 7/06 (2013.01); B32B 7/12 (2013.01); B32B 27/06 (2013.01); B32B 27/16 (2013.01); C08L 33/14 (2013.01); C09J 133/14 (2013.01); G02F 1/167 (2013.01); *B29C 39/02* (2013.01); *B29C 2059/023* (2013.01); *B32B 2307/20* (2013.01); *B32B 2457/20* (2013.01); *B32B 2457/202* (2013.01); *G02F 2001/1672* (2013.01)

(58) Field of Classification Search
CPC ... G02F 1/167; G02F 1/1334; C08L 2666/02; C08L 75/06; C08L 2666/18; C08L 51/006; C08L 53/00; C08L 53/02; C08L 67/04; C08L 33/06; C08L 33/14; C08G 18/792; C08G 18/10; C08G 18/12; C08G 18/5066; C08G 18/50; C08G 18/0866; C08G 18/5015; C08G 18/5039; C08G 18/8038; C08G 18/8087; C08G 18/3206; C08G 18/482; C08G 18/6674; C08G 18/672; C08G 2190/00; C09J 153/00; C09J 151/006; C09J 153/02
USPC ........... 428/156, 1.5, 166, 172, 1.1, 1.2, 1.54, 428/1.55, 411.1, 72, 73, 913
See application file for complete search history.

(56) References Cited

U.S. PATENT DOCUMENTS

| 5,908,899 A * | 6/1999 | Tahara et al. ................. 525/301 |
| 6,327,072 B1 * | 12/2001 | Comiskey et al. ............ 359/296 |
| 6,750,844 B2 * | 6/2004 | Nakanishi .................... 345/107 |
| 6,788,449 B2 * | 9/2004 | Liang et al. .................... 359/296 |
| 6,829,078 B2 * | 12/2004 | Liang et al. .................... 359/296 |
| 6,833,943 B2 * | 12/2004 | Liang et al. .................... 359/296 |
| 6,930,818 B1 | 8/2005 | Liang et al. |
| 6,933,098 B2 * | 8/2005 | Chan-Park ............. G02F 1/167 204/453 |
| 7,112,114 B2 * | 9/2006 | Liang et al. ..................... 445/24 |
| 7,141,279 B2 * | 11/2006 | Liang et al. ..................... 428/1.5 |
| 7,158,282 B2 * | 1/2007 | Liang et al. .................... 359/296 |
| 7,684,108 B2 | 3/2010 | Wang et al. |
| 7,715,088 B2 * | 5/2010 | Liang et al. .................... 359/296 |
| 7,830,592 B1 | 11/2010 | Sprague et al. |
| 7,880,958 B2 * | 2/2011 | Zang ................. C08G 18/3814 345/107 |
| 8,023,071 B2 * | 9/2011 | Liang et al. ...................... 349/86 |
| 8,237,892 B1 | 8/2012 | Sprague et al. |
| 8,361,356 B2 * | 1/2013 | Zang et al. ..................... 264/4.1 |
| 2002/0176963 A1 * | 11/2002 | Chen ....................... G02F 1/167 428/156 |
| 2004/0170776 A1 * | 9/2004 | Liang ................ G02F 1/133377 428/1.2 |
| 2004/0219306 A1 * | 11/2004 | Wang ..................... C08G 18/10 428/1.5 |
| 2007/0036919 A1 * | 2/2007 | Wang ..................... C08G 18/10 428/1.54 |
| 2007/0237962 A1 * | 10/2007 | Liang ..................... G02F 1/167 428/411.1 |
| 2008/0020007 A1 * | 1/2008 | Zang ............................. 424/401 |
| 2009/0059347 A1 | 3/2009 | Hiraoka et al. |
| 2009/0231245 A1 | 9/2009 | Lin |
| 2010/0033803 A1 * | 2/2010 | Wang et al. .................... 359/296 |

FOREIGN PATENT DOCUMENTS

| WO | WO 01/67170 | 9/2001 |
| WO | WO 2008091520 A1 * | 7/2008 ........... C08G 18/672 |
| WO | WO 2012-033376 A2 | 3/2012 |
| WO | WO 2012-152392 A1 | 11/2012 |

OTHER PUBLICATIONS

Allen, K. (Oct. 2003). Electrophoretics Fulfilled. *Emerging Displays Review: Emerging Display Technologies, Monthly Report*—Oct. 2003, 9-14.
Bardsley, J.N. & Pinnel, M.R. (Nov. 2004) Microcup™ Electrophoretic Displays. *USDC Flexible Display Report*, 3.1.2. pp. 3-12-3-16.
Chaug, Y.S., Haubrich, J.E., Sereda, M. and Liang, R.C. (Apr. 2004). Roll-to-Roll Processes for the Manufacturing of Patterned Conductive Electrodes on Flexible Substrates. *Mat. Res. Soc. Symp. Proc.*, vol. 814, I9.6.1.
Chen, S.M. (Jul. 2003) The Applications for the Revolutionary Electronic Paper Technology. *OPTO News & Letters*, 102, 37-41. (in Chinese, English abstract attached).

(Continued)

*Primary Examiner* — Robert A Wax
*Assistant Examiner* — Olga V Tcherkasskaya
(74) *Attorney, Agent, or Firm* — Perkins Coie LLP

(57) ABSTRACT

The present invention is directed to a composition for preparing the microcups and the toughness of the display panel formed from such a composition may be significantly improved. In some cases, the panel may have an elongation at break of more than 10% and it can be completely peeled off from the substrate layer on which it is formed, without causing any damage to the panel.

10 Claims, 9 Drawing Sheets

(56) References Cited

OTHER PUBLICATIONS

Chen, S.M. (May 2003) The New Application and the Dynamics of Companies. *TRI.* 1-10. (In Chinese, English abstract attached).

Chung, J., Hou, J., Wang, W., Chu, L.Y., Yao, W., & Liang, R.C. (Dec. 2003). Microcup® Electrophoretic Displays, Grayscale and Color Rendition. *IDW*, AMD2/EP1-2, 243-246.

Ho, Andrew. (Nov. 2006) *Embedding e-Paper in Smart Cards, Pricing Labels & Indicators.* Presentation conducted at Smart Paper Conference Nov. 15-16, 2006, Atlanta, GA, USA.

Ho, C., & Liang, R.C. (Dec. 2003). *Microcup® Electronic Paper by Roll-to-Roll Manufacturing Processes.* Presentation conducted at FEG, Nei-Li, Taiwan.

Ho, Candice. (Feb. 1, 2005) *Microcupt® Electronic Paper Device and Application.* Presentation conducted at USDC 4th Annual Flexible Display Conference 2005.

Hou, J., Chen, Y., Li, Y., Weng, X., Li, H. and Pereira, C. (May 2004). Reliability and Performance of Flexible Electrophoretic Displays by Roll-to-Roll Manufacturing Processes. *SID Digest*, 32.3, 1066-1069.

Lee, H., & Liang, R.C. (Jun. 2003) SiPix Microcup® Electronic Paper—An Introduction. *Advanced Display*, Issue 37, 4-9 (in Chinese, English abstract attached).

Liang, R.C. (Feb. 2003) *Microcup® Electrophoretic and Liquid Crystal Displays by Roll-to-Roll Manufacturing Processes.* Presentation conducted at the Flexible Microelectronics & Displays Conference of U.S. Display Consortium, Phoenix, Arizona, USA.

Liang, R.C. (Apr. 2004). *Microcup Electronic Paper by Roll-to-Roll Manufacturing Process.* Presentation at the Flexible Displays & Electronics 2004 of Intertech, San Fransisco, California, USA.

Liang, R.C. (Oct. 2004) *Flexible and Roll-able Displays/Electronic Paper—A Technology Overview.* Paper presented at the METS 2004 Conference in Taipei, Taiwan.

Liang, R.C., & Tseng, S. (Feb. 2003).*Microcup® LCD, A New Type of Dispersed LCD by A Roll-to-Roll Manufacturing Process.* Paper presented at the IDMC, Taipei, Taiwan.

Liang, R.C., (Feb. 2005) *Flexible and Roll-able Displays/Electronic Paper—A Brief Technology Overview.* Flexible Display Forum, 2005, Taiwan.

Liang, R.C., Hou, J., & Zang, H.M. (Dec. 2002) Microcup Electrophoretic Displays by Roll-to-Roll Manufacturing Processes. *IDW*, EP2-2, 1337-1340.

Liang, R.C., Hou, J., Chung, J., Wang, X., Pereira, C., & Chen, Y. (May 2003). Microcup® Active and Passive Matrix Electrophoretic Displays by A Roll-to-Roll Manufacturing Processes. *SID Digest*, vol. 34, Issue 1, pp. 838-841, 20.1.

Liang, R.C., Hou, J., Zang, H.M., & Chung, J. (Feb. 2003). *Passive Matrix Microcup® Electrophoretic Displays.* Paper presented at the IDMC, Taipei, Taiwan.

Liang, R.C., Hou, J., Zang, H.M., Chung, J., & Tseng, S. (Feb. 2003). Microcup® Displays: Electronic Paper by Roll-to-Roll Manufacturing Processes. *Journal of the SID*, 11(4), 621-628.

Liang, R.C., Zang, H.M., Wang, X., Chung, J. & Lee, H., (Jun./Jul. 2004) ‹ Format Flexible Microcup® Electronic Paper by Roll-to-Roll Manufacturing Process ›, Presentation conducted at the 14th FPD Manufacturing Technology Expo & Conference.

Nikkei Microdevices. (Dec. 2002) Newly-Developed Color Electronic Paper Promises—Unbeatable Production Efficiency. *Nikkei Microdevices*, p. 3. (in Japanese, with English translation).

Sprague, R.A. (Sep. 23, 2009) SiPix Microcup Electrophoretic Epaper for Ebooks. *NIP 25*, 2009 pp. 460-462. (Presentation conducted on Sep. 23, 2009 at the 25th Int'l Conference on Digital Printing Technologies, Digital Fabrication 2009 (NIP 25) by Society for Imaging Science and Technology, in Louisville, Kentucky, USA.).

Wang, X., Kiluk, S., Chang, C., & Liang, R.C. (Feb. 2004). Mirocup® Electronic Paper and the Converting Processes. *ASID*, 10.1.2-26, 396-399, Nanjing, China.

Wang, X., Kiluk, S., Chang, C., & Liang, R.C., (Jun. 2004) Microcup® Electronic Paper and the Converting Processes. *Advanced Display*, Issue 43, 48-51 (in Chinese, with English abstract).

Wang, X., Zang, H.M. and Li, P. (Jun. 2006) Roll-to-Roll Manufacturing Process for Full Color Electrophoretic film. *SID Digest*, 2006, pp. 1587-1589.

Zang, H.M, Hwang, J.J., Gu, H., Hou, J., Weng, X., Chen, Y., et al. (Jan. 2004). Threshold and Grayscale Stability of Microcup® Electronic Paper. *Proceeding of SPIE-IS&T Electronic Imaging, SPIE* vol. 5289, 102-108.

Zang, H.M. & Hou, Jack, (Feb. 2005) *Flexible Microcup® EPD by RTR Process.* Presentation conducted at $2^{nd}$ Annual Paper-Like Displays Conference, Feb. 9-11, 2005, St. Pete Beach, Florida.

Zang, H.M. (Oct. 2003). *Microcup® Electronic Paper by Roll-to-Roll Manufacturing Processes.* Presentation conducted at the Advisory Board Meeting, Bowling Green State University, Ohio, USA.

Zang, H.M. (Feb. 2004). *Microcup Electronic Paper.* Presentation conducted at the Displays & Microelectronics Conference of U.S. Display Consortium, Phoenix, Arizona, USA.

Zang, H.M. (Sep. 2006) *Monochrome and Area Color Microcup® EPDs by Roll-to-Roll Manufacturing Process.* Presentation conducted at the Fourth Organic Electronics Conference and Exhibition (OEC-06), Sep. 25-27, 2006, Frankfurt, Germany.

Zang, H.M. (Feb. 2007) *Developments in Microcup® Flexible Displays.* Presentation conducted at the 6th Annual Flexible Display and Microelectronics Conference, Phoenix, AZ Feb. 6-8.

Zang, H.M., & Liang, R.C. (2003) Microcup Electronic Paper by Roll-to-Roll Manufacturing Processes. *The Spectrum*, 16(2), 16-21.

Zang, H.M., Wang, F., Kang, Y.M., Chen, Y. and Lin, W. (Jul. 2007) *Microcup® e-Paper for Embedded and Flexible Designs.* IDMC'07, Taipei International Convention Center, Taiwan.

Zang, H.M., Wang, W., Sun, C., Gu, H., and Chen, Y. (May 2006) Monochrome and Area Color Microcup® EPDs by Roll-to-Roll Manufacturing Processes. *ICIS' 06 International Congress of Imaging Science Final Program and Proceedings*, pp. 362-365.

Patent Cooperation Treaty, PCT/US2013/069902, PCT Notification of Transmittal of the International Search Report and the Writteen Opinion of the International Searching Authority, or The Declaration, Mailed on Mar. 6, 2014.

\* cited by examiner

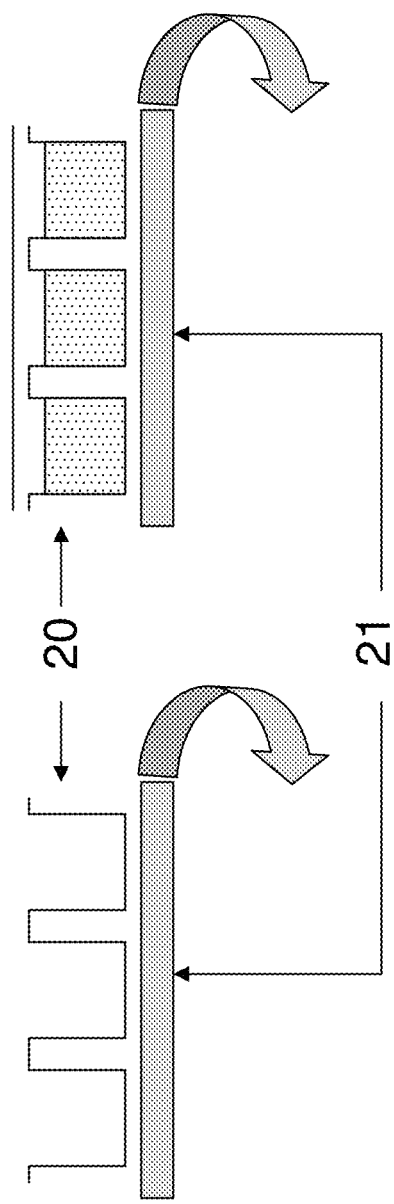

MICROCUP COMPOSITIONS

BACKGROUND

U.S. Pat. No. 6,930,818 describes the microcup technology for forming a display panel. According to the patent, microcups may be formed by either a batchwise process or a continuous roll-to-roll process. A composition for forming the microcups is first coated on a substrate layer, followed by a microembossing or photolithographic method. A preferred process is microembossing by applying a male mold over the microcup composition to form microcups. The microcup composition can also be coated onto the male mold, followed by applying a substrate layer on top. The male mold may be released during or after the microcup composition is hardened.

The display panel formed is normally a very thin layer and therefore fragile. Once it is formed on a substrate layer, the microcup layer is very difficult to be peeled off from the substrate layer without causing damage to the structure.

Prior to the present invention, a release layer was considered to be added between a display panel and a substrate layer, to facilitate separation of the display panel, if needed, from the substrate layer after the display panel is formed on the substrate layer. However, this approach had its disadvantages. For example, the formation of the microcups by microembossing could become difficult. This is due to the fact that when pulling the mold from the partially cured microcups, with the presence of a release layer between the display panel and the substrate layer, the layers could be prematurely separated. Moreover, the mold could also get stuck in the partially cured microcups to cause permanent damage to the mold.

Another possible approach was to increase the thickness of the bottom of the microcups, so that the microcups can withstand the peel force for separating the display panel from the substrate layer and avoid causing damage to the display panel. However in this case, the thicker microcup bottom will cause more voltage drop at the microcup bottom, which likely leads to insufficient voltage for driving a display fluid contained within the microcups.

A further possible approach was to increase the thickness of the partition walls separating the microcups. However, increasing the thickness of the walls will decrease the fill factor, resulting in unsatisfactory optical performance.

SUMMARY OF THE INVENTION

One aspect of the invention is directed to a display panel comprising a plurality of microcups filled with a display fluid and sealed with a sealing layer, which panel has a greater than 10% elongation at break. In one embodiment, the panel has a greater than 20% elongation at break.

Another aspect of the invention is directed to a display panel comprising (a) a plurality of microcups filled with a display fluid and sealed with a sealing layer, and (b) a primer layer, which panel has a greater than 5% elongation at break. In one embodiment, the display panel has a greater than 15% elongation at break.

A further aspect of the invention is directed to a composition for forming microcups, which comprises:
 (a) at least one difunctional UV curable component;
 (b) at least one photoinitiator; and
 (c) at least one mold release agent.

In one embodiment, the difunctional UV curable component has a molecular weight higher than about 200. In one embodiment, the difunctional UV curable component is a difunctional acrylate. In one embodiment, the difunctional acrylate has an urethane or ethoxylated backbone. In one embodiment, the difunctional UV curable component is diethylene glycol diacrylate, triethylene glycol diacrylate, tetraethylene glycol diacrylate, polyethylene glycol diacrylate, polyethylene glycol dimethacrylate, ethoxylated bisphenol A diacrylate, ethoxylated bisphenol A dimethacrylate or urethane diacrylate.

In one embodiment, the photoinitiator is bis-acyl-phosphine oxide, 2-benzyl-2-(dimethylamino)-1-[4-(4-morpholinyl)phenyl]-1-butanone, 2,4,6-trimethylbenzoyl diphenyl phosphine oxide, 2-isopropyl-9H-thioxanthen-9-one, 4-benzoyl-4'-methyldiphenylsulphide and 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propane-1-one, 2,2-dimethoxy-1,2-diphenylethan-1-one or 2-methyl-1[4-(methylthio)phenyl]-2-morpholinopropan-1-one.

In one embodiment, the mold release agent is an organo-modified silicone copolymer.

In one embodiment, the composition further comprises a co-initiator. In one embodiment, the composition further comprises a monofunctional UV curable component. In one embodiment, the composition further comprises a multifunctional UV curable component. In one embodiment, the composition further comprises a stabilizer.

Yet a further aspect of the invention is directed to a device comprising a plurality of microcups formed from a composition of the present invention, wherein the microcups are filled with a functional material composition and sealed with a sealing layer. In one embodiment, the functional material composition is in the form of a liquid, such as an electrophoretic fluid. In one embodiment, the functional material is a medicinal or cosmetic agent. In one embodiment, the device further comprises a primer layer.

Yet a further aspect of the invention is directed to a method for the preparation of a display device, which method comprises:
 (a) forming a display panel comprising a plurality of microcups from a composition of the present invention on a substrate layer, filling the microcups with a display fluid and sealing the filled microcups;
 (b) separating the display panel from the substrate layer; and
 (c) laminating electrode layers onto both sides of the display panel.

Yet a further aspect of the invention is directed to a method for the preparation of a piezo display device, which method comprises:
 (a) forming a display panel comprising a plurality of microcups from a composition of the present invention on a first substrate layer, filling the microcups with a display fluid and sealing the filled microcups;
 (b) separating the display panel from the first substrate layer;
 (c) cutting the display panel into pieces of any dimensions before or after step (b);
 (d) transferring the pieces of the display panel onto a second substrate layer with gaps between the pieces of display panel; and
 (e) filling the gaps with a piezo material.

BRIEF DESCRIPTION OF THE DRAWINGS

FIGS. 2a and 2b show the separation of a display panel from a substrate layer.

DETAILED DESCRIPTION OF THE INVENTION

The present inventors have now found a composition for preparing microcups and the toughness of the panel formed from such a composition may be significantly improved. In some cases, a panel formed from such a composition may have an elongation at break of more than 10% and the panel formed from it can be completely peeled off from a substrate layer on which it is formed, without causing any damage to the panel. The term "elongation at break" or "elongation", in the context of the present invention, is expressed as a percentage increase in length before one or both of the following two conditions occur (i) the loss of structural integrity of the microcups, such as cracks or fissures becoming visually detectable, or (ii) the leak of the liquid component filled in the microcups becoming visually detectable.

In the context of the present application, the term "panel" refers to a layer of microcups, filled with a functional material composition (usually in a liquid form) and hermetically sealed with a sealing layer. The panel does not include a substrate layer. The panel, however, may include one or more dielectric layers, such as a layer of a binder material, a layer of a matrix material, an adhesive layer, a primer layer or any one of other electrode-protecting layers, to provide support to the functional material contained in the microcups. The panel may include a conductor layer sandwiched in between the dielectric layers or exposed on the outside.

Figure 1A:
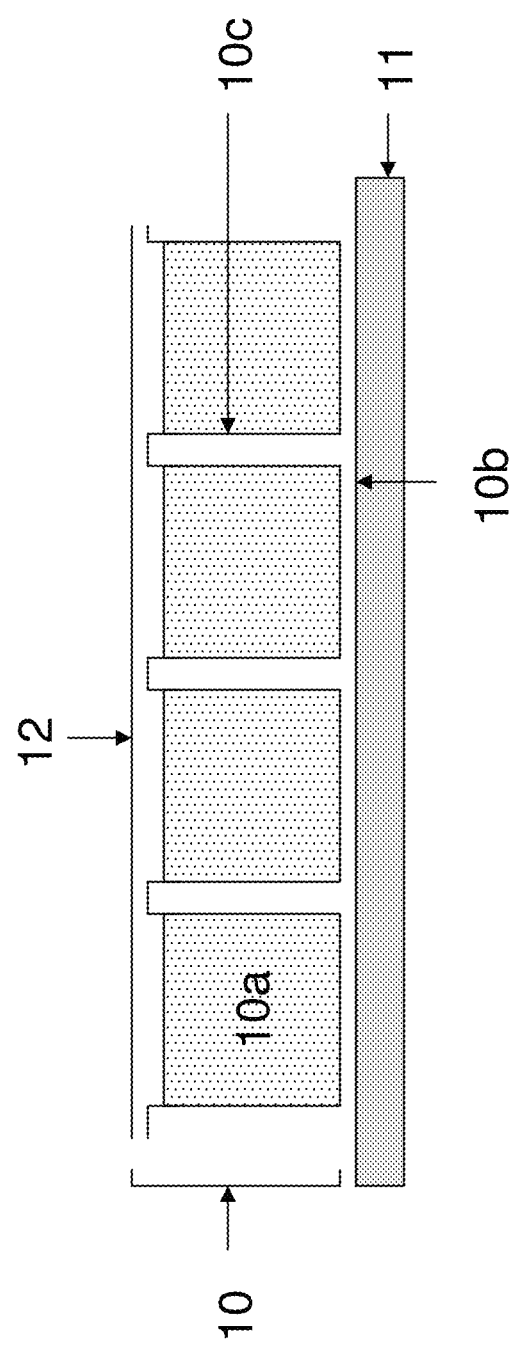
FIGS. 1a and 1b depict general structures of microcup-based panel on a substrate layer.

FIG. 1a depicts a microcup-based panel on a substrate layer. As shown, a panel (10) comprising microcups (10a) formed on a substrate layer (11). It is optional to have a microcup bottom (10b) which is formed from the same composition as the microcup walls (10c). In the process of forming the panel, the microcups are filled with a functional material composition. The functional material composition may be a display fluid, a pharmaceutical composition or the like.

If it is a display fluid, the fluid may be an electrophoretic fluid comprising charged pigment particles dispersed in a solvent or solvent mixture.

The filled microcups are then sealed with a sealing layer (12) following a one-pass or two-pass procedure, according to U.S. Pat. No. 6,930,818. In the one-pass method, a sealing composition is pre-dispersed into a composition of a functional material and the dispersion of the two compositions is coated onto the microcups. The sealing composition is hardened during or after it floats to the top of the functional material composition. In the "two-pass" method, a functional material composition and a sealing composition are sequentially coated into the microcups, followed by hardening the sealing composition. In either method, the sealing composition and the functional material composition are preferably immiscible. The hardening of the sealing composition occurs in situ (i.e., the sealing composition is being hardened when on top of the functional material composition.)

The content of U.S. Pat. No. 6,930,818 is incorporated herein by reference in its entirety.

Figure 1B:
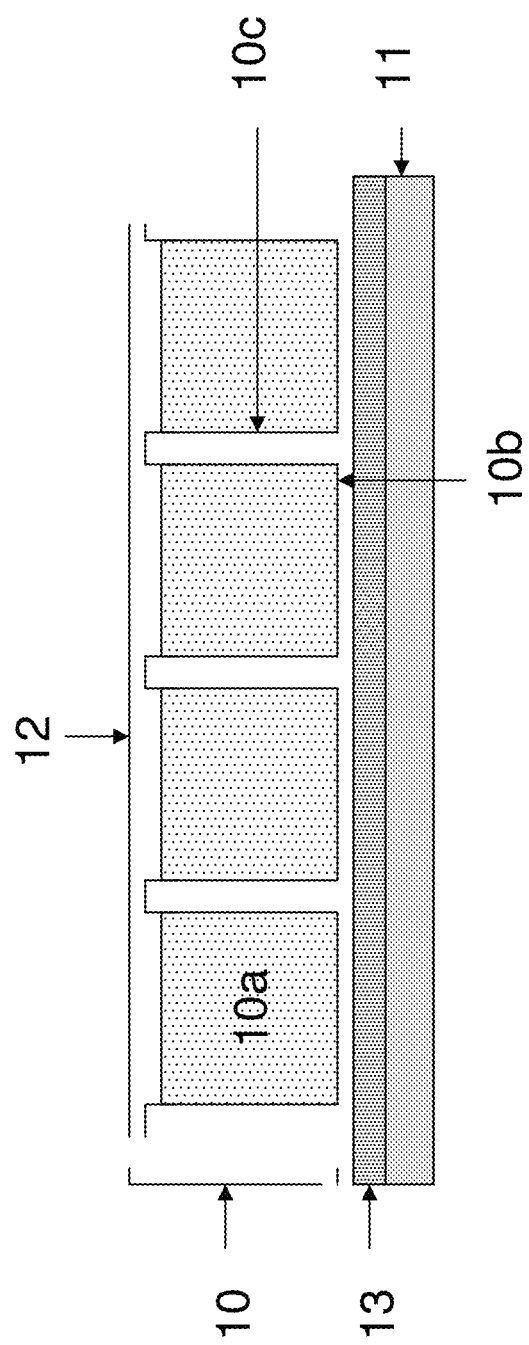

There may be a primer layer (13) adjacent to the panel, as shown in FIG. 1 *b*.

The composition of the present invention comprises (a) at least one difunctional UV curable component, (b) at least one photoinitiator, and (c) at least one mold release agent.

a. Difunctional UV Curable Component

The total percentage of the difunctional UV curable component(s) in the composition may range from about 10 wt % to about 99 wt %, preferably from about 30 wt % to about 99 wt % and more preferably from about 50 wt % to about 99 wt %. The difunctional UV curable component has two reactive function groups.

Suitable difunctional components for the present invention may have a molecular weight higher than about 200. Difunctional acrylates are preferred and difunctional acrylates having an urethane or ethoxylated backbone are particularly preferred.

More specifically, suitable difunctional components may include, but are not limited to, diethylene glycol diacrylate (e.g., SR230 from Sartomer), triethylene glycol diacrylate (e.g., SR272 from Sartomer), tetraethylene glycol diacrylate (e.g., SR268 from Sartomer), polyethylene glycol diacrylate (e.g., SR295, SR344 or SR610 from Sartomer), polyethylene glycol dimethacrylate (e.g., SR603, SR644, SR252 or SR740 from Sartomer), ethoxylated bisphenol A diacrylate (e.g., CD9038, SR349, SR601 or SR602 from Sartomer), ethoxylated bisphenol A dimethacrylate (e.g., CD540, CD542, SR101, SR150, SR348, SR480 or SR541 from Sartomer), and urethane diacrylate (e.g., CN959, CN961, CN964, CN965, CN980 or CN981 from Sartomer; binding agents for coating sold under EBECRYL® 230, EBECRYL® 270, EBECRYL® 8402, EBECRYL® 8804, EBECRYL® 8807 or EBECRYL® 8808 from Cytec).

b. Photoinitiator

The total percentage of the photoinitiator(s) in the composition may range from about 0.1 wt % to about 5 wt % and preferably from about 0.4 wt % to about 2 wt %.

Suitable photoinitiators may include, but are not limited to, bis-acyl-phosphine oxide, 2-benzyl-2-(dimethylamino)-1-[4-(4-morpholinyl)phenyl]-1-butanone, 2,4,6-trimethylbenzoyl diphenyl phosphine oxide, 2-isopropyl-9H-thioxanthen-9-one, 4-benzoyl-4'-methyldiphenylsulphide and 1-hydroxycyclohexyl-phenyl-ketone, 2-hydroxy-2-methyl-1-phenylpropan-1-one, 1-[4-(2-hydroxyethoxy)-phenyl]-2-hydroxy-2-methyl-1-propane-1-one, 2,2-dimethoxy-1,2-diphenylethan-1-one or 2-methyl-1 [4-(methylthio)phenyl]-2-morpholinopropan-1-one.

c. Mold Release Agent

The percentage of the mold release agent in the composition may range from about 1 wt % to about 10 wt % and preferably from about 2 wt % to about 6 wt %.

Suitable mold release agents may include, but are not limited to, organomodified silicone copolymers such as silicone acrylates (e.g., binding agents for coating sold under EBECRYL® 1360 or EBECRYL® 350 from Cytec), silicone polyethers (e.g., Silwet 7200, Silwet 7210, Silwet 7220, Silwet 7230, Silwet 7500, Silwet 7600 or Silwet 7607 from Momentive).

The composition may further optionally comprise one or more of the following components, a co-initiator, monofunctional UV curable component, multifunctional UV curable component or stabilizer.

d. Co-Initiator

Co-initiator can be added to the composition to overcome oxygen inhibition and improve surface curing speed. The percentage of the co-initiator in the composition may range from 0 wt % to about 20 wt % and preferably from about 5 wt % to about 10 wt %.

Suitable co-initiators may include, but are not limited to, amine functionalized acrylates, such as CN371, CN373, CN384US or CN386US from Sartomer.

e. Monofunctional UV Curable Component

In the context of the present application, the term, "monofunctional", is referred to as having one reactive function group.

The percentage of the monofunctional UV curable components in the composition may range from 0 wt % to about 80 wt % and preferably from 0 wt % to about 40 wt %.

Suitable monofunctional UV curable components may include, but are not limited to, methyl methacrylate, methyl acrylate, ethyl methacrylate, ethyl acrylate, n-butyl acrylate, n-butyl methacrylate, lauryl methacrylate, lauryl acrylate, 2-ethylhexyl methacrylate, 2-ethylhexyl acrylate, methacrylic acid, acrylic acid, hydroxyethyl methacrylate, hydroxyethylacrylate, styrene or acrylate monomers from Sartomer, such as CD551, CD553, CD611, CD9087, CD9088, SR256 or SR504.

f. Multifunctional UV Curable Component

In the context of the present application, the term, "multifunctional", is referred to as having more than two reactive function groups.

The percentage of the multifunctional UV curable components in the composition may range from 0 wt % to about 80 wt % and preferably from 0 wt % to about 40 wt %.

Suitable multifunctional UV curable components may include, but are not limited to, trifunctional acrylates or methacrylates (e.g., CD501, SR 415, SR444, SR454, SR499, SR502, CN972 or SR9035 from Sartomer), tetra- or pentafunctional acrylates or methacrylates (e.g., SR295, SR355, SR399, SR494 or SR9041 from Sartomer), trifunctional urethane acrylates (e.g., CN929 from Sartomer) or hexfunctional polyester acrylates (e.g., a binding agent for coating sold under EBECRYL® 830 from Cytec).

g. Stabilizer

Stabilizers can be added into the microcup composition to ensure long term thermal and photo durability of the composition after curing. The percentage of the stabilizers in the composition may range from 0 wt % to about 10 wt % and preferably from 0 wt % to about 5 wt %. Suitable stabilizers may include, but are not limited to, phenolic-, amino-, sulphur-based and multifunctional antioxidants, such as the antioxidants sold under IRGANOX® series supplied by BASF.

The microcups utilizing the present composition may be prepared by microembossing, filled and sealed, as described in U.S. Pat. No. 6,930,818.

The microcup layer (20) prepared from the present composition may be easily separated without damage, from a substrate layer (21) before filling as shown in FIG. 2a or after filling and sealing as shown in FIG. 2b.

As stated above, there may be a primer layer adjacent the panel. The primer layer is optional.

If the primer layer is extremely thin (e.g., <1 um) or no primer layer at all, the mechanical strength of the panel preferably has a >10% elongation and more preferably a >20% elongation, after curing.

If the primer layer is relatively thick (e.g., 1~10 um), the mechanical strength of the panel derived from the microcup composition described above may have a >5% elongation and preferably a >15% elongation, after curing. The overall mechanical strength for the panel and the primer layer has to meet a >5% elongation and preferably a >10% elongation, after curing.

The composition of a primer layer, if present, is at least partially compatible with the microcup composition of the present invention, after curing.

For example, the primer layer may be formed from a composition comprising a polar oligomeric or polymeric material. Such a polar oligomeric or polymeric material may be selected from the group consisting of oligomers or polymers having at least one of the groups such as nitro ($-NO_2$), hydroxyl ($-OH$), carboxyl ($-COO$), urethane ($-NH-C(O)-O$), urea ($NH-C(O)-NH$), alkoxy ($-OR$ wherein R is an alkyl group), halo (e.g., fluoro, chloro, bromo or iodo), cyano ($-CN$), sulfonate ($-SO_3$) or the like.

The glass transition temperature of the polar polymer material is preferably below about 100° C. and more preferably below about 60° C.

The primer layer formed from such a composition preferably has an average crosslinking density of below about 1 crosslink point per 80 molecular weight and more preferably below about 1 crosslink point per 120 molecular weight. The suitable crosslinking density can be achieved by incorporating polar polymeric materials or polar oligomeric materials of different molecular weights in the composition. For example, a polar oligomer having a relatively high molecular weight may be blended with another polar oligomer having a low molecular weight to achieve a desired crosslinking density.

Examples of suitable polar oligomer may include, but are not limited to, polyhydroxy functionalized polyester acrylates (such as BDE 1025 from Bomar Specialties Co, Winsted, Conn.) or alkoxylated acrylates, such as ethoxylated nonyl phenol acrylate (e.g., SR504 from Sartomer Company), ethoxylated trimethylolpropane triacrylate (e.g., SR9035 from Sartomer Company) or ethoxylated pentaerythritol tetraacrylate (e.g., SR494 from Sartomer Company).

Examples of suitable polar polymers may include, but not limited to urethane polymers, such as thermoplastic polyurethane polymers sold under IROSTIC®.

The polar oligomeric or polymeric material is compatible with other components in the composition and can be easily processed by simple mixing.

The weight percentage of the polar oligomeric or polymeric material in the composition for the primer layer may be no less than about 1%, preferably no less than about 3% and most preferably no less than about 10%.

With such a composition, the primer layer having an intended volume resistivity of about 1/1000 to about 100 times that of an electrophoretic fluid filled in the microcups may be achieved. The primer layer may have an intended volume resistivity of about $10^7$ to about $10^{12}$ ohm cm at 25° C. and 40% relative humidity.

Optionally, an adhesion promoter can be added to the primer layer composition to ensure good adhesion to the microcup structure. Such adhesion promoters may include, but are not limited to, carboxylated acrylates, hydroxylated acrylate, metal acrylates and the like, preferably at a concentration of about 0.1 wt % to about 15 wt %.

Optionally, a photo-initiator for UV curing may also be added in the primer layer composition, if UV curing is desired.

The panel of the present invention may be utilized in a variety of ways. A few examples are provided below.

a) Display Device

In the case where the microcups are filled with a display fluid (e.g., an electrophoretic fluid), the panel may utilized as shown in the following examples.

Figure 3:
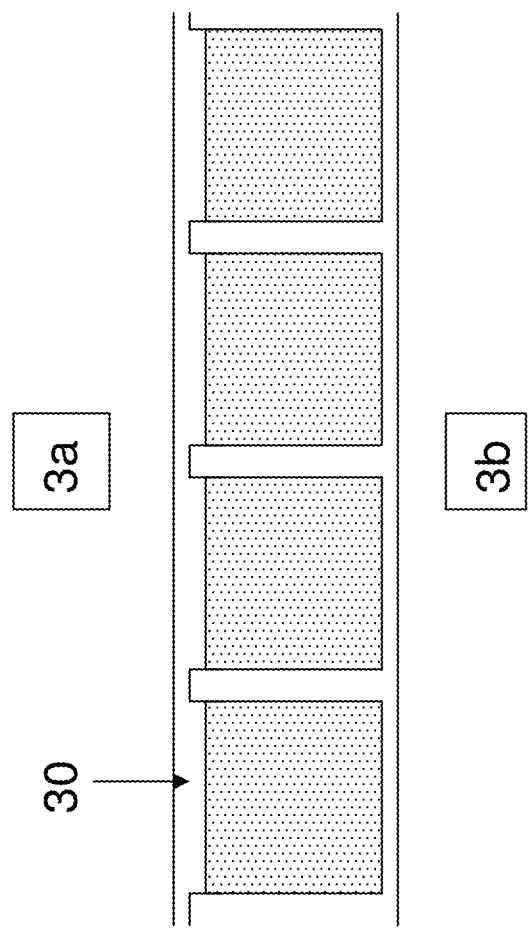
FIG. 3 depicts a panel of the present invention.

A panel as shown in FIG. 3 has a sealing layer (30) side (3a) and a non-sealing layer side (3b). Either side may be the viewing side in a display device.

Figure 4:
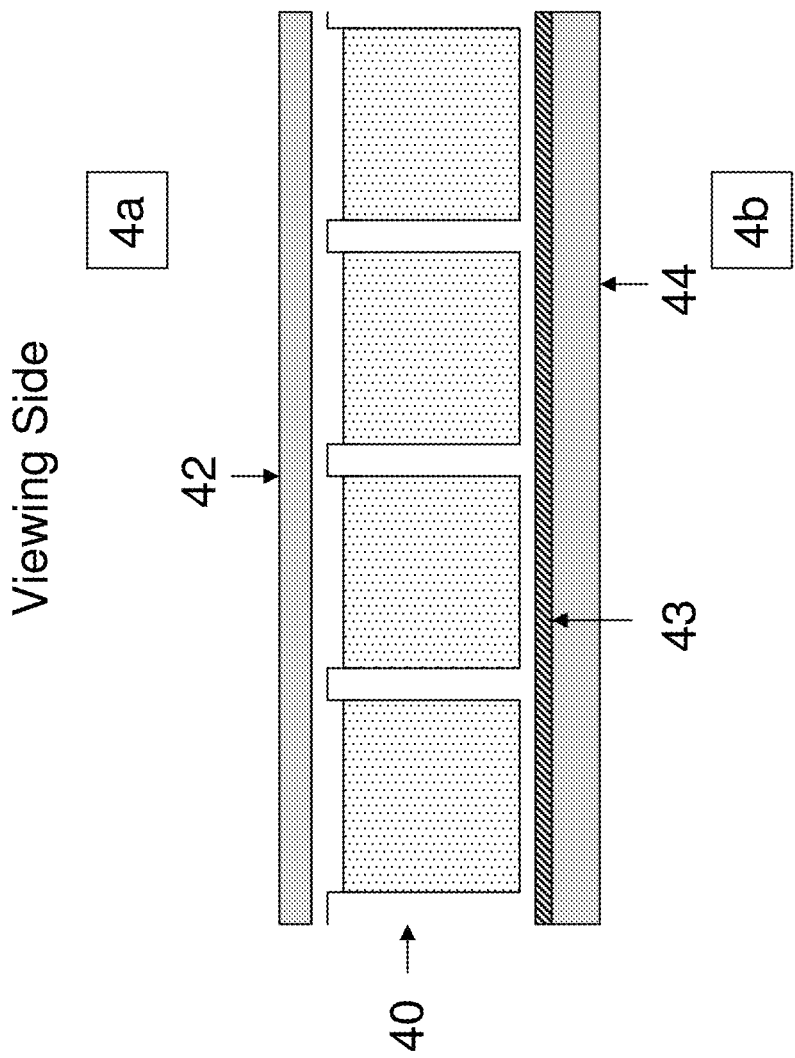
FIGS. 4 and 5 illustrate a display device formed from a panel.

In FIG. 4, the sealing layer side (4a) is the viewing side. In this case, a transparent electrode layer (42) is directly deposited or transferred onto the sealing layer side of the panel (40). The transparent electrode layer may be, but are not limited to, ITO (indium tin oxide), carbon nano tube, PEDOT [poly(3, 4-ethylenedioxythiophene)] or silver nano wire. In this assembly, on the opposite side (with or without a primer layer), an adhesive layer (43) is added in order for a backplane (44) to be attached to the panel.

Figure 5:
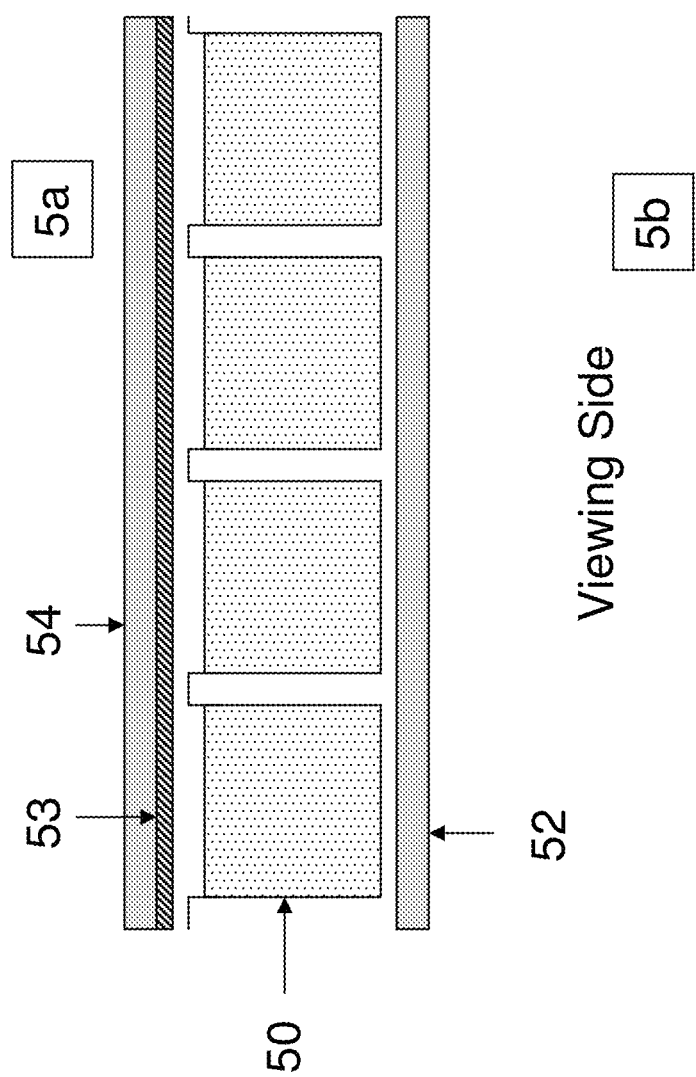

In FIG. 5, the non-sealing layer side (5b) is the viewing side. In this case, a transparent electrode layer (52) is directly deposited or transferred onto the panel (50) or onto a primer layer if there is a primer layer. In this assembly, an adhesive layer (53) is added onto the sealing layer side (5a) in order for a backplane (54) to be attached to the panel.

For the display assembly of FIG. 4 or 5, it is driven by the voltage potential difference between the transparent electrode layer and the backplane.

There is an option to directly deposit or transfer an electrode layer onto both sides of the panel to from a simple single pixel display or low resolution segment display. The electrode on the viewing side has to be transparent. The electrode on the back side (non-viewing side) can be opaque and made out of conductive inks (such as silver ink or carbon black ink) which can be directly printed onto the panel for forming a segment display.

Figure 6:
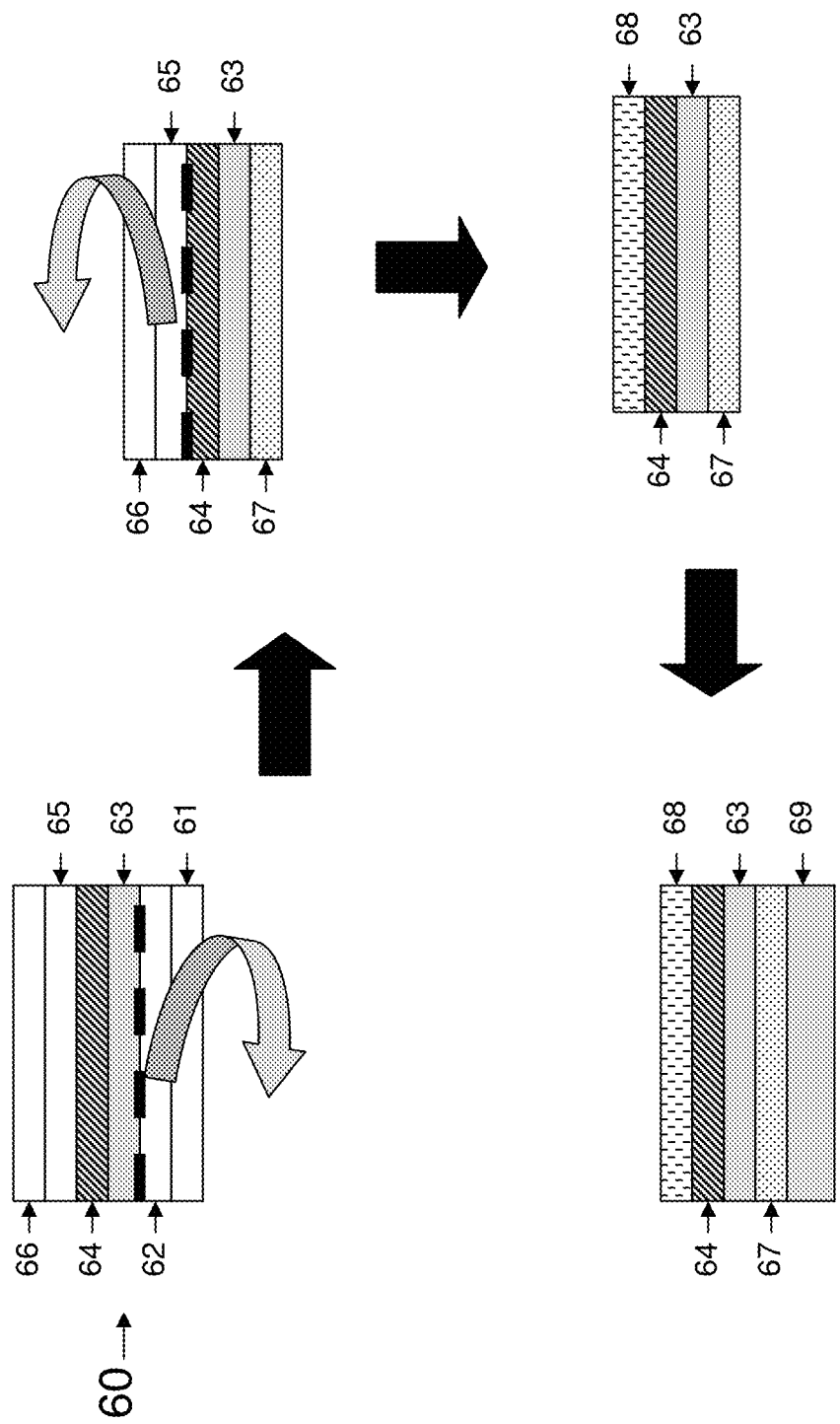
FIG. 6 illustrates an alternative route of forming a display device from a panel.

In a further example as shown in FIG. 6, a stack (60) of layers is assembled. In the stack, there are a first substrate layer (61), a first release layer (62), an electrode layer (63), an adhesive layer (64), a second release layer (65) and a second substrate layer (66). In assembling a display device, the first substrate layer (61) and the first release layer (62) are removed and a microcup panel (67) of the present invention is laminated over the electrode layer (63). In another step which may be carried out before or after the removal of the first substrate layer and the first release layer, the second substrate layer (66) and the second release layer (65) are removed, followed by adding an auxiliary layer (68) through the adhesive layer (64). The auxiliary layer may be a luminance enhancement layer as described in U.S. Ser. No. 12/323,300 filed on Nov. 25, 2008, U.S. Ser. No. 12/323,315 filed on Nov. 25, 2008 and U.S. Ser. No. 12/397,917 filed on Mar. 4, 2009, color filters, anti-glare layer, anti-scratch layer or the like. On the other side, a backplane (69) is laminated to the panel (67) to complete the display device.

Figure 7:
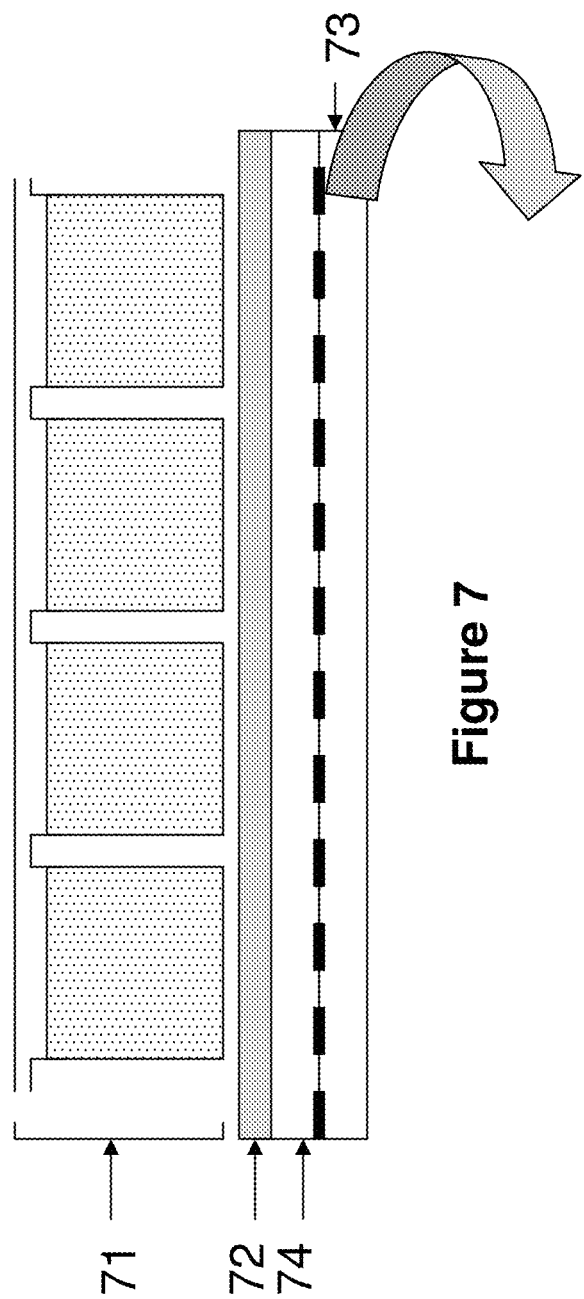
FIG. 7 shows an electrode layer along with a panel is removed from a substrate layer.

FIG. 7 depicts yet a further example. In this example, a microcup panel (71) is formed on an electrode layer (72) which is associated with a substrate layer (73). While the panel is peeled off, the electrode layer will stay with the panel instead of the substrate layer. This can be accomplished by carefully selecting a substrate layer having an optimal surface energy between the substrate layer and the electrode layer. In this case, ITO is not preferred as the electrode layer due to its cracking behavior under stress. Preferred electrode layer may be silver nano wire, carbon nano tube, conductive polymers, such as PEDOT or the like. Optionally, there is a protection layer (74) adjacent to the electrode layer to protect the electrode layer during separation and post processing.

It is also possible to have a primer layer adjacent to the panel. In this example, the panel, the primer layer and the electrode layer will be together while peeled off from the substrate layer.

In yet a further example, a release layer may be present between the panel and a substrate layer to further facilitate the separation. If a primer layer is present between the panel and the substrate layer, the primer layer adjacent to the panel can also be released from the substrate layer with ease.

Figure 8:
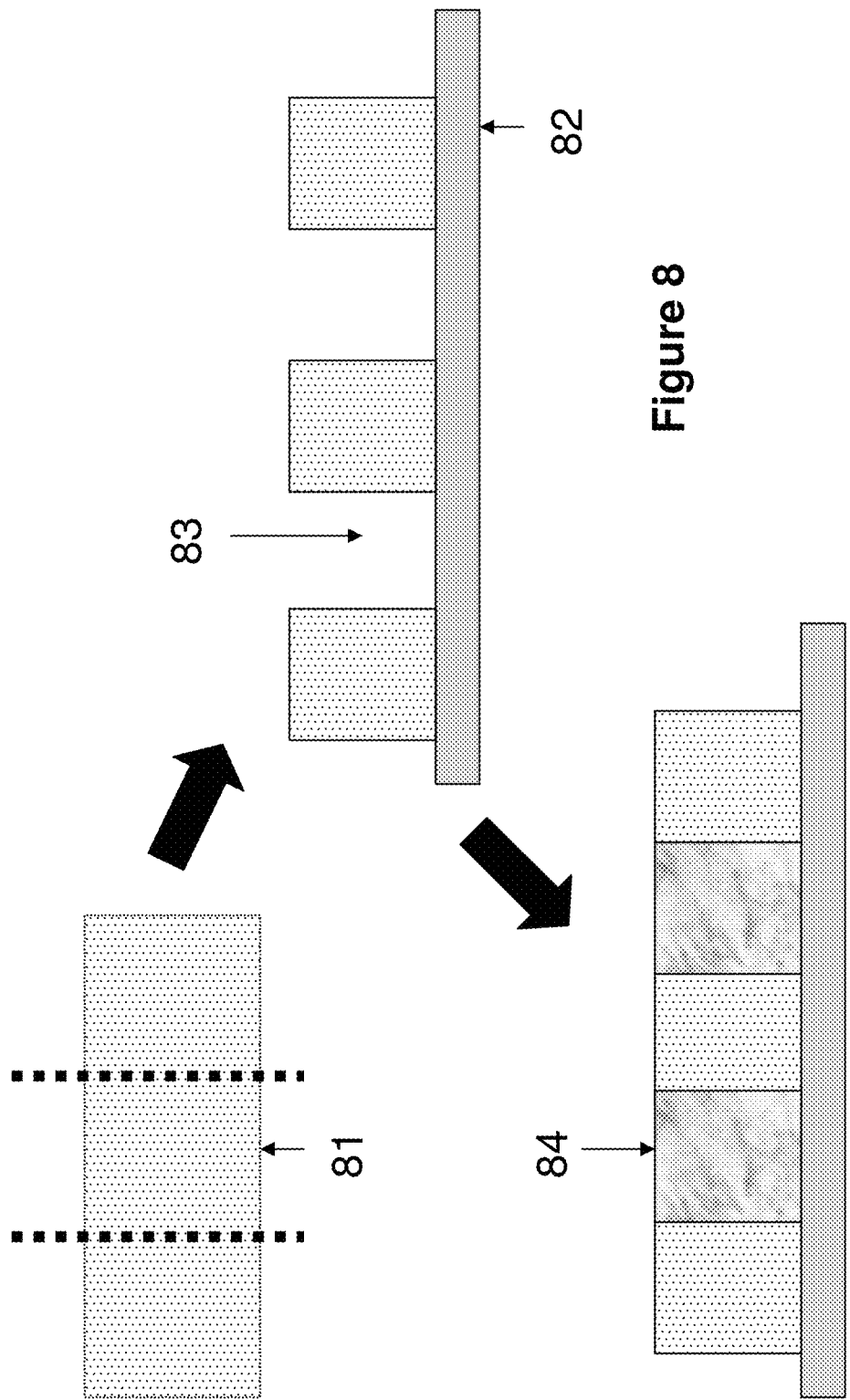
FIG. 8 illustrates the use of a panel in forming a piezo display device.

In a further example as shown in FIG. 8, a display panel of the present invention, after being separated from the substrate layer on which the panel is formed, may be transferred to another substrate layer. In one embodiment, a panel (81) may be cut into any dimensions before being transferred to another substrate layer (82), and in this case, there may be gaps (83) left between the pieces of the panel on the substrate layer (82) and the gaps may be filled with a non-display material (84), such as a piezo material.

b) Transdermal Delivery Device

The panel may also be used for pharmaceutical applications, in particular used in a transdermal delivery device (e.g., plaster or patch). Such a delivery device may be used for local or systemic drug delivery. The pharmaceutical composition filled in the microcups may comprise an active ingredient which may be a medicinal or cosmetic agent. The medicinal agent may include substances intended for use in the diagnosis, cure, mitigation, treatment or prevention of diseases, or to affect the structure or function of the body. The medicinal agent may be a single chemical entity or a pharmaceutically acceptable salt thereof which will be present in an amount such that the device delivers a therapeutically effective amount for the disease or condition being treated. The amount that constitutes a therapeutically effective amount will vary, according to the type of the medicinal agent used, the condition to be treated, any medicinal agents being co-administered, the amount of time the composition is allowed to remain in contact with the skin of the patient, and other factors known to those of skill in the art.

The active ingredient present in the pharmaceutical composition will generally be about 0.01 wt % to about 40 wt %, preferably about 1.0 wt % to about 20 wt %, based on the total weight of the composition.

Any drug that is suitable for transdermal delivery can be used in the panel of the present invention. Examples of useful drugs include, but are not limited to, anti-inflammatory drugs, antibacterials, antiprotozoals, antifungals, coronary vasodilators, calcium channel blockers, bronchodilators, enzyme inhibitors, antihypertensives, anti-ulceratives, steroidal hormones, antivirals, immunomodulators, local anesthetics, antitussives, antihistamines, narcotic analgesics, peptide hormones, sex hormones, enzymes, antinauseants, anticonvulsants, immunosuppressives, psychotherapeutics, sedatives, anticoagulants, analgesics, antiarrhythmics, antiemetics, contraceptives, anticancer agents, neurologic agents, hemostatics, anti-obesity agents, smoking cessation regimens or the like.

The composition for pharmaceutical applications may also comprise excipients, such as a solvent, cosolvent, solubilizer, solvent modifier, permeation enhancer, preservative, buffering agent or the like. The solvent is the principal component of the composition and preferably is one in which the active ingredient is soluble or at least substantially soluble or can be made soluble or become soluble, by addition of a cosolvent or solvent modifier. Suitable solvents may be selected from any of the solvents normally used for medicaments, cosmetics, nutrients or other active agents to be delivered transdermally. Preferred solvents include lower alcohols of from 2 to 6 carbon atoms, preferably from 2 to 4 carbon atoms and may be monoalcohols, such as, ethanol, isopropanol or sec-butanol, or polyols, such as, ethylene glycol, propylene glycol, butylene glycol or glycerol. A mixture of solvents may also be used. Other solvents, such as ketone (e.g., acetone or methylethyl ketone), ethers (e.g., ethylether) may also be used, in an amount which will be safe and non-toxic. While the solvent system is generally non-aqueous, water may be used for water soluble active ingredients and for those active ingredients which are stable in the presence of and not denigrated by the presence of water. When water is present in the solvent, in some cases, it will usually constitute less than about 50 wt %, preferably less than about 10 wt %, more preferably less than about 2 wt %, by weight of the total solvent although more or less may be used, depending on the active ingredient and as long as the objective of the invention can be met.

Generally, the total amount of solvent(s) will be selected to assure dissolution of the active ingredient and excipients and provide suitable product viscosity. The amount of solvent(s) falling within the range of from about 5 wt % to about 90 wt %, preferably from about 25 wt % to about 75 wt %, based on the total composition, may be used.

The composition filled in the microcups preferably is in the form of a solution. However it is also possible to be in form of a suspension/dispersion, emulsion, gel or the like.

For transdermal delivery applications, the active ingredient permeates through the sealing layer at a desired rate. Diffusion of the active ingredient through the sealing layer is dependent on properties of the active ingredient, the solvent in which the active ingredient is present, the chemical nature of the sealing layer/adhesive layer or any other layers in between the active ingredient and the skin. The rate of diffusion, in general, tends to decrease with increased molecular volume. The rate of skin penetration, on the other hand, is a function of the diffusion coefficient, the barrier partitioning tendency, binding affinity and the rate of metabolism of the active ingredient by the skin. The sealing layer, in this application, is preferably a continuous or microporous film. A continuous film may be prepared from, for example, ethylene:vinyl acetate copolymers which may contain an appropriate amount of vinyl acetate, for example, about 0.5 wt % to about 40 wt %.

The panel formed on a substrate is removed (peeled off) from the substrate layer on which it is formed and it is then transferred to another film layer. The film layer, such as, an elastic bandage coated with a pressure sensitive adhesive, is more flexible than the substrate layer on which the panel is formed, and therefore more suitable to be applied to skin for proper delivery of the pharmaceutical composition in the panel.

EXAMPLES

Example 1 (Comparative)

Microcup Composition without Difunctional Components 39.6 Parts by weight of a binding agent for coating sold under EBECRYL® 830 (Cytec), 51 parts of SR-399 (Sartomer), 7 parts of a binding agent for coating sold under EBECRYL® 1360 (Cytec), 0.2 parts of 2,4,6-trimethylbenzoyl diphenyl phosphine oxide and 2.2 parts of 1-hydroxycyclohexyl-phenyl-ketone were mixed homogeneously and used in the tensile strength test.

Example 2

Microcup Composition with Difunctional Components

21 Parts by weight of a binding agent for coating sold under EBECRYL® 8808 (Cytec), 39.7 parts of SR-602 (Sartomer), 25 parts of CD9038 (Sartomer), 4 parts of Silwet 7607 (Momentive), 9.86 parts of CN373 (Sartomer), 0.2 parts of 4-benzoyl-4'-methyldiphenylsulphide, and 0.24 parts of 2,4,6-trimethylbenzoyl diphenyl phosphine oxide were mixed homogeneously and used for the tensile test.

Example 3

Tensile Test of Cured Microcup Materials

The microcup compositions of Examples 1 and 2 were coated onto 5 mil PET film with a targeted dry thickness of about 100 um, covered by PET release film, and then cured for 20 seconds under UV light at an intensity of 5 mW/cm$^2$. The PET cover sheet was removed. The cured microcup layer was peeled off from the PET substrate and cut into stripes with a width of 1.25 cm and a length of 10 cm. The tensile test was then conducted by Instron at 50 mm/min. The results listed in Table 1 were the average of at least 5 measurements. The microcup composition containing difunctional components showed much improved elongation at break and toughness.

TABLE 1

|  | Example 1 | Example 2 |
| --- | --- | --- |
| Tensile Strength (N/m$^2$) | $8.25 \times 10^6$ | $3.95 \times 10^6$ |
| Elongation at Break (%) | 1.31 | 22.86 |
| Toughness (J/m$^3$) | $5.37 \times 10^6$ | $45.43 \times 10^6$ |

Example 4

Tensile Test of Panel

The microcup composition of Example 2 was used to prepare the microcup array with a thickness of around 27 um by microembossing according to U.S. Pat. No. 6,930,818. The electrophoretic fluid comprising charged pigment particles dispersed in a hydrocarbon solvent was coated onto the microcup array on a ITO/PET substrate film. The filled microcups are then sealed with a sealing layer with a thickness of around 17 um, following a one-pass procedure, according to U.S. Pat. No. 6,930,818. The microcup-based panel was then peeled off from the ITO/PET substrate film and subjected to the tensile test as described in Example 3.

The elongation was measured to be 18% before the microcup structure was damaged.

This same test could not be carried out with the microcup composition of Example 1 because the panel prepared from the composition of Example 1 could not be separated from the ITO/PET substrate film, without causing damages to the panel.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, materials, compositions, processes, process step or steps, to the objective, spirit and scope of the present invention. All such modifications are intended to be within the scope of the claims appended hereto.

It is therefore wished that this invention to be defined by the scope of the appended claims as broadly as the prior art will permit, and in view of the specification.

What is claimed is:

1. A display panel comprising a plurality of microcups filled with a display fluid and sealed with a sealing layer, wherein the microcups are formed from a composition comprising at least one difunctional UV curable diacrylate or dimethacrylate material selected from the group consisting of diethylene glycol diacrylate, triethylene glycol diacrylate, tetraethylene glycol diacrylate, polyethylene glycol diacrylate, ethoxylated bisphenol A diacrylate, urethane diacrylate, ethoxylated bisphenol A dimethacrylate, and polyethylene glycol dimethacrylate, the total amount of the at least one difunctional UV curable diacrylate or dimethacrylate material is about 50-99% by weight of the composition, and the display panel has a greater than 10% elongation at break.

2. The display panel of claim 1, which has a greater than 20% elongation at break.

3. A display panel comprising (a) a plurality of microcups filled with a display fluid and sealed with a sealing layer, and (b) a primer layer, wherein the microcups are formed from a composition comprising at least one difunctional UV curable diacrylate or dimethacrylate material selected from the group consisting of diethylene glycol diacrylate, triethylene glycol diacrylate, tetraethylene glycol diacrylate, polyethylene glycol diacrylate, ethoxylated bisphenol A diacrylate, urethane diacrylate, ethoxylated bisphenol A dimethacrylate, and polyethylene glycol dimethacrylate, the total amount of the at least one difunctional UV curable diacrylate or dimethacrylate material is about 50-99% by weight of the total composition, and the display panel has a greater than 5% elongation at break.

4. The display panel of claim 3, which has a greater than 15% elongation at break.

5. A display device comprising the display panel of claim 1.

6. The device of claim 5, wherein the display fluid is an electrophoretic fluid.

7. The device of claim 5, further comprising a primer layer.

8. The display panel of claim 1, wherein the display fluid is an electrophoretic fluid.

9. The display panel of claim 1, wherein the difunctional UV curable diacrylate or dimethacrylate material has a molecular weight higher than about 200 daltons.

10. The display panel of claim 1, wherein the microcups are formed from ethoxylated bisphenol A diacrylate or urethane diacrylate.

* * * * *